(12) United States Patent
Mabotuwana et al.

(10) Patent No.: US 9,904,966 B2
(45) Date of Patent: Feb. 27, 2018

(54) USING IMAGE REFERENCES IN RADIOLOGY REPORTS TO SUPPORT REPORT-TO-IMAGE NAVIGATION

(71) Applicants: Thusitha Dananjaya De Silva Mabotuwana, Yonkers, NY (US); Yuechen Qian, Briarcliff Manor, NY (US)

(72) Inventors: Thusitha Dananjaya De Silva Mabotuwana, Yonkers, NY (US); Yuechen Qian, Briarcliff Manor, NY (US)

(73) Assignee: Koninklijke Philips N.V.

( * ) Notice: Subject to any disclaimer, the term of this patent is extended or adjusted under 35 U.S.C. 154(b) by 652 days.

(21) Appl. No.: 14/211,653

(22) Filed: Mar. 14, 2014

(65) Prior Publication Data

US 2014/0278554 A1    Sep. 18, 2014

Related U.S. Application Data

(60) Provisional application No. 61/782,524, filed on Mar. 14, 2013.

(51) Int. Cl.
| | | |
|---|---|---|
| G06F 17/20 | (2006.01) | |
| G06Q 50/24 | (2012.01) | |
| G06Q 10/10 | (2012.01) | |
| G06F 19/00 | (2018.01) | |
| G06F 17/28 | (2006.01) | |
| G06F 17/27 | (2006.01) | |

(52) U.S. Cl.
CPC .......... *G06Q 50/24* (2013.01); *G06F 19/321* (2013.01); *G06F 19/3487* (2013.01); *G06Q 10/10* (2013.01); *G06F 17/2775* (2013.01)

(58) Field of Classification Search
CPC ...... G06Q 50/24; G06Q 10/10; G06F 19/321; G06F 19/3487; G06F 17/2775
USPC .......................... 704/4, 231, 251, 260, 276
See application file for complete search history.

(56) References Cited

U.S. PATENT DOCUMENTS 7,899,684 B2 * 3/2011 Fukatsu .............. G06F 19/3406
705/2

FOREIGN PATENT DOCUMENTS

WO    WO 2011132097 A2 * 10/2011 ........... G06F 19/321

\* cited by examiner

*Primary Examiner* — Thierry L Pham

(57) ABSTRACT

A system, method and computer readable storage medium for retrieving a narrative report for at least one study including a plurality of images of a patient from a memory, determining text structure boundaries to identify and classify each text structure in the narrative report, determining image references in each text structure of the narrative report, extracting image references from text structures classified as including an image reference and determining a study to which an extracted image reference corresponds.

14 Claims, 3 Drawing Sheets

USING IMAGE REFERENCES IN RADIOLOGY REPORTS TO SUPPORT REPORT-TO-IMAGE NAVIGATION

On a routine basis, radiologists have to work with an increasing number of imaging studies to diagnose and treat patients in an optimal manner. Patients, especially ones with cancers, undergo frequent imaging exams and over time, accumulate many studies reports in their medical records. Each time a new study is read, the radiologist would typically open one or more prior radiology reports to establish the patient's clinical context. A similar practice can also be observed by consumers of the radiology reports such as, for example, oncologists and referring physicians.

In the radiology workflow, after a patient has had an imaging study performed using, for example, X-ray, CT, MRI, the images are transferred to the Picture Archiving and Communications system (PACS) using Digital Imaging and Communications in Medicine (DICOM) standards. Radiologists read images stored in PACS and generate a radiology report generally using a reporting software. The report is then transferred to the PACS or Radiology Information System (RIS) depending on the specific hospital configuration via Health Level 7 (HL7) standards. The radiology reports are narrative n nature and typically contain several institution specific section headers such as, for example, Clinical Information to give a brief description of the reason for the study, Comparison to refer to a relevant prior study, Findings to describe what has been observed in the images and Impressions which contain diagnostic details and follow-up recommendations.

Oftentimes, the radiology reports also contain references to specific images when describing finding. For example, "Neurofibroma in the superior right extraconal space (series 5, image 104) measuring approximately 17 mm." In the current workflow, if a radiologist also wants to look at the images referenced in a prior report to better understand the progression of findings, the only option is to manually open the prior study in the PACS system, then open the series of interest (e.g., series 5), and then navigate to the corresponding image slice (e.g., image 104). An imaging study may have multiple series (i.e., sequences). For example, an abdomen study may contain multiple series such as axial, coronal and sagittal series and series with dedicated window-level settings. A series in turn may contain multiple images. For example, MRI studies may contain several hundred images. Navigating to a specific image manually is a time consuming, laborious process and as a result, users may be reluctant to navigate to the referenced image(s), resulting in a possible compromise in quality.

Figure 1:
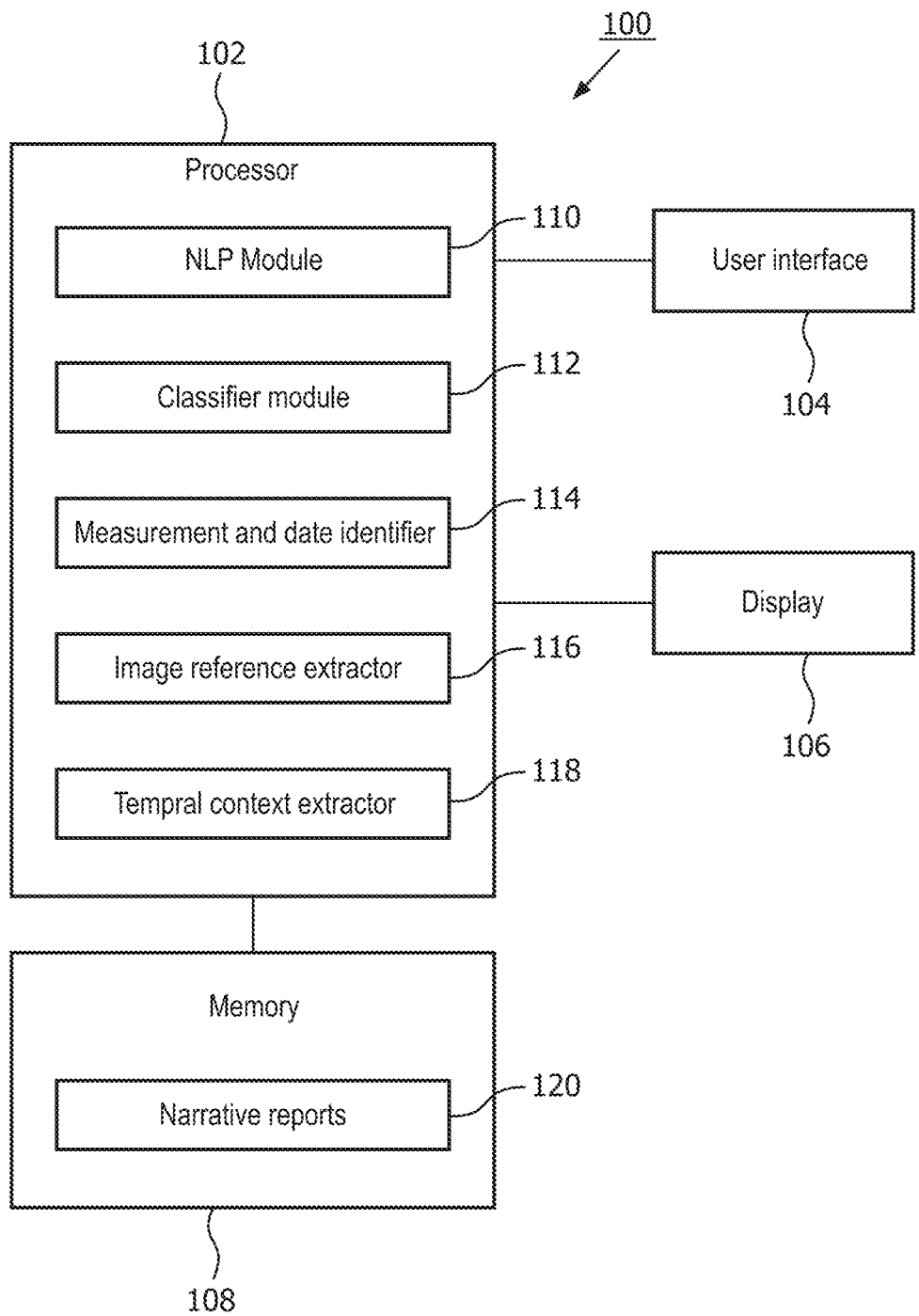
FIG. 1 shows a schematic drawing of a system according to an exemplary embodiment.

The exemplary embodiments may be further understood with reference to the following description and the appended drawings, wherein like elements are referred to with the same reference numerals. The exemplary embodiments relate to a system and method for reviewing a medical image. In particular, the exemplary embodiments describe a system and method for extracting image references from free-text radiology reports to support enhanced report-to-image navigation. Although the exemplary embodiments are specifically described in regard to reviewing images of cancer patients within a radiology department, it will be understood by those of skill in the art that the system and method of the present disclosure may be used for patients having any of a variety of diseases or conditions within any of a variety of hospital departments.

It is noted that the exemplary embodiments are described with reference to sentences. However, those skilled in the art will understand that the same principles and functionalities described herein may be applied to text structures that have more or less context than a sentence. For example, the exemplary embodiments may be applied to a text structure that has less context such as a phrase or a text structure that has more context such as the entirety of a multi-sentence paragraph (e.g., a paragraph that is not broken into its constituent sentences).

As shown in FIG. 1, a system 100 according to an exemplary embodiment of the present disclosure automatically extracts image references from narrative text reports 118 to enhance report-to-image navigation. The system 100 comprises a processor 102, a user interface 104, a display 106 and a memory 108. The processor 102 extracts image references from narrative text reports 120 of a patient stored in the memory 108 such that a user (e.g., radiologist) may easily navigate from a report to an image. It will be understood by those of skill in the art that the memory 108 may be any computer-readable storage medium. Once image references have been extracted from the text reports 120, the processor 102 may generate a diagnostic report, which may be displayed on the display 106. The diagnostic report may include, for example, hyperlinks to images referenced in the patient reports 120 such that the user may select a hyperlink to open a corresponding image in the correct study and series. User selections may be made via the user interface 104, which may include input devices such as, for example, a keyboard, mouse and/or touch display on the display 106. It will be understood by those of skill in the art that the system 100 generates a custom diagnostic report specific to each patient. It will also be understood by those of skill in the art that the system 100 may be a personal computer, a server, or any other known processing arrangement.

The processor 102 extracts image references from the narrative text reports 120 by using, for example, a Natural Language Processing (NLP) Module 110 to determine sentence boundaries. The NLP module 110 determines sentence boundaries by recognizing sections, paragraphs and sentences in narrative reports via end-of-sentence markers such as, for example, periods, colons, exclamations marks, question marks and return functions. These end-of-sentence markers are used to classify portions of text into one of a sentence-identifying label. Once the sentences are extracted, a classifier module 112 determines whether a sentence contains one or more image references by recognizing image identifying terms, number formats and/or other identifying information. It should be noted that the classifier module 112 is an optional module. As described herein, the classifier module 112 is a filtering module that separates sentences that have image references from sentences that do not have image references. If the classifier module 112 is used, the image reference extractor module 116 (which operation is described below) may operate only on those sentences that are classified as including the image references. However, it is also possible to not classify the sentences and have the image reference extractor module 116 operate on all the sentences.

The processor 102 also includes a measurement and date identifier 114 to distinguish measurement/date values from image references. Once the measurement/date values have been distinguished from the image references, the processor 102 uses an image reference extractor module 116 to extract the image references and a temporal context extractor module 118 to determine the study to which the image reference belongs.

Figure 2:
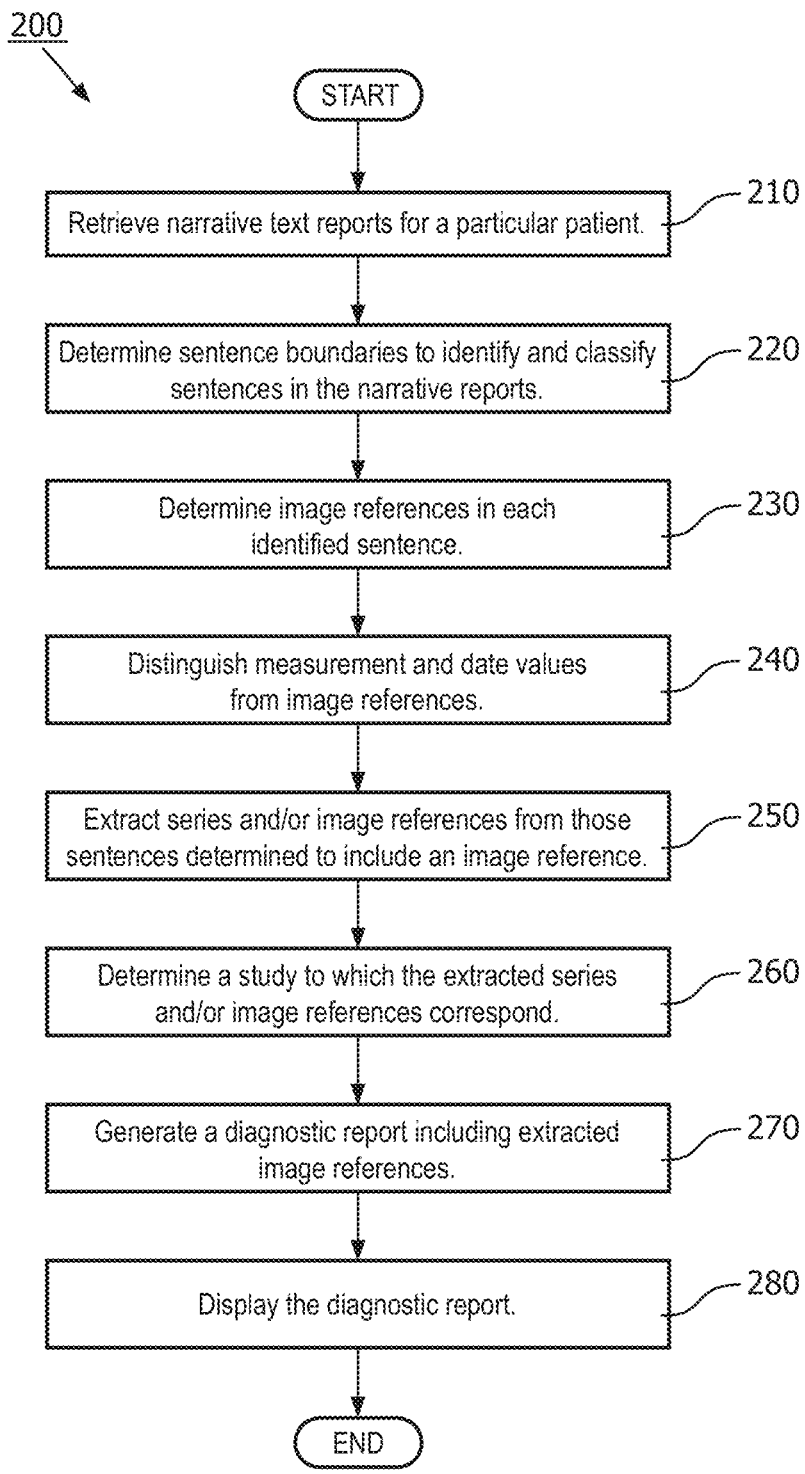
FIG. 2 shows a flow diagram of a method according to an exemplary embodiment.

FIG. 2 shows a method 200 via which the system 100 extracts image references from narrative text reports 120 to generate a diagnostic report. To support report-to-image navigation, it is necessary to not only to extract image references, but also to determine which study the image reference is on. For example, in cases in which a prior date or reference to a prior study is not explicitly identified, it may be determined that the reference is on the current study. As described above, the exemplary embodiments perform this extraction at a sentence level, but it is also possible to perform the extraction at a lower level of context or a higher level of context. For any particular implementation, a sample of random narrative text reports may be examined to determine the different ways in which radiologists refer to specific images. The varying references to images may be used to determine classifier features which identify image references for the particular implementation.

In a step 210, the system 100 retrieves the narrative text reports 120 for a particular patient. In a step 220, the processor 102 determines sentence boundaries using, for example, the NLP module 110. The NLP module 110 may recognize sections, paragraphs and sentences in the narrative reports 120. The NLP module 110 may be implemented as a maximum entropy classifier that assigns an end-of-sentence marker in one of a sentence-identifying label. The end-of-sentence marker may include, for example, periods, colons, exclamations, question marks and carriage returns. The sentence-identifying labels may include, for example, (i) not end of sentence; (ii) end of sentence, and sentence is a section header; (iii) end of sentenced, and sentence is the last sentence in a paragraph; and (iv) end of sentence and neither of the above classes. Using this classification, the entire section-paragraph-sentence structure can be reconstructed.

Once the sentences have been extracted, in a step 230, the processor 102 determines if a sentence contains one or more image references using, for example, the classifier module 112. The classifier module 112 may include features which, for example, recognize whether a sentence includes the term "image" followed by a number, includes the term "series" followed by a number, includes the term "series", includes a number over a number (e.g., 5/131), has planar information (e.g., axial), and/or has a measurement or a date. The classifier module 112 may be implemented using regular expressions and may be augmented by extending the above features to ignore variations in terms as well as punctuation (e.g., image, images, on image number 45, etc.). As noted above, step 230 and the classifier module 112 are optional. The method 200 may be performed without step 230.

In step 240, the processor 102 distinguishes measurement and date values from image references using, for example, the measurement and date identifier 114. The measurement and date identifier 114 may mark those references which are deemed to be measurement and/or date values such that these marks can be used to disambiguate between an image reference and a date or a measurement. Radiologists may often include references to measurements and dates in the same sentence as image references. For example, the radiologist may note " . . . nodule is unchanged compared to prior exam (series 8; image 14; 20 Sep. 2003 study)." In this case, the measurement and date identifier 114 will determine that the referenced image is 14, instead of ignoring punctuations and extracting images 14-20 or images 14 and 20. The measurement and date identifier 114 may utilize regular expressions to determine and mark the commonly used ways of representing measurements and dates such as, for example, 5 mm or 5×3 mm for measurements and 10 Jul. 2011, Dec. 20, 2010 or 5 Dec. 2009 for dates.

After measurement and date values are marked in the step 240, series and image references are extracted in step 250. Series and image references may be extracted using the image reference extractor 116, which utilizes a rule-based approach implemented using regular expressions. In an exemplary embodiment, the image reference extractor 116 includes four primary rules. The first rule extracts references where both the series and image information are explicitly provided along with one or more numeric values (e.g., series 55, images 45, 46 and 48; image number 14 on series 20; image 50/series 4; series 4, image 43, image 44; series 3 image 125/152; coronal series 5, image 33). The second rule may be similar to the first, but a series can be referred to using a scanning plane (e.g., coronal image 118; axial image 5/44 and axial images 5-12). The third rule extracts information from sentences that contain series related information (e.g., via the word "series" or reference to a scanning plane), but do not contain "image" along with the corresponding numeric values (e.g., series 80254/48; coronal/35 and 280; series 8). The fourth rule looks for a pattern of number-over-number, not matched by any of the prior rules. For example, a sentence may state "left lower lobe has increased in size, measuring 2×1.6 cm (5/131). By convention, the first number is interpreted as the particular image number (e.g., 5) and the second number is the total number of image reference (e.g., 131), if the first number is less than the second number. Similarly, the result may be interpreted as series/image if the first number is greater than the second number. For example, a sentence may state "enlarged right hilar lymphadenopathy measuring 11 mm (80232/49). In order to minimize false positives, the fourth rule may be limited to image values and/or number slices out of date ranges. For example, 11/25 may not be matched by this rule. It will be understood by those of skill in the art that a sentence can contain multiple image references matching multiple rules. For example, two references will be extracted from a sentence which states "2.3×2.3 by 2-cm (5/49, coronal/35) lobulated nodule in the left lower lobe" using the fourth and third rules described above.

For each case in which the image reference extractor 116 extracts one or more image references, the processor 102 determines the study the image belongs to, in a step 260. The corresponding study may be determined by, for example, using the temporal context extractor 118. In some cases, the image reference corresponds to the current study. In other cases, however, the radiologist may refer to images in prior studies such that the image reference corresponds to a prior study. The temporal context extractor 118 may identify (i) keywords such as "scan" and "study" in conjunction with dates occurring prior to an image reference (e.g., "On the 12/19/10 scan as measured on series 2 image 120 . . . "); (ii) the presence of a date after an image reference (e.g., " . . . white matter signal increase (series 601 image 44 on 3 Jun. 2010) is not as clearly seen today"); (iii) terms such as "prior" and "previous" occurring before or after the image reference (e.g., . . . "measures 3 mm (series 4, image 52)", "previously 4 mm (series 4, image 32)" and "on image 17 series 4 of prior study"). In another example of determining the study an image reference belongs to, may be to determine the study from the 'Comparison' section that is a section that commonly appears in radiology reports. For example, if the sentence contains " . . . in prior study . . . " without explicitly specifying the image/series, the prior study may still be determined.

Figure 3:
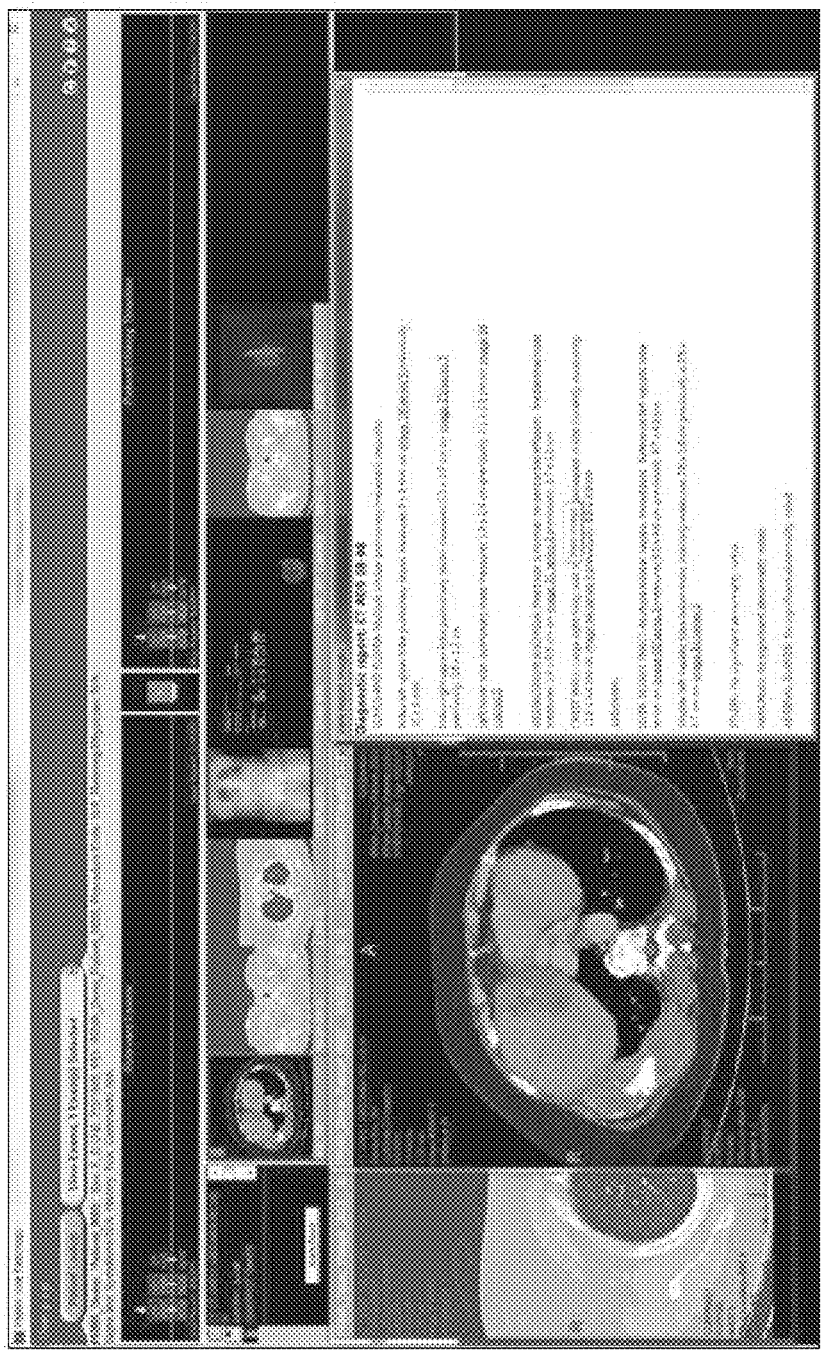
FIG. 3 shows an exemplary screen shot of a diagnostic report and image windows displayed according to the method of FIG. 2.

In a step 270, the processor 102 generates a custom diagnostic report for the patient based on image references extracted from the narrative free text reports 120 for that patient. In a step 280, the generated diagnostic report may be displayed on the display 106, as shown in FIG. 3. The diagnostic report may include one or more hyperlinks to referenced images such that, when the user selects a hyperlink via the user interface 104, a window showing the corresponding image may also be displayed on the display 106. A user may select more than one hyperlink to open one or more windows showing corresponding images.

It is noted that the claims may include reference signs/numerals in accordance with PCT Rule 6.2(b). However, the present claims should not be considered to be limited to the exemplary embodiments corresponding to the reference signs/numerals.

Those skilled in the art will understand that the above-described exemplary embodiments may be implemented in any number of manners, including, as a separate software module, as a combination of hardware and software, etc. For example, the NLP module 110, the classifier module 112, the measurement and date identifier 114, the image reference extractor 116 and the temporal context extractor 118 may be programs containing lines of code that, when compiled, may be executed on a processor.

It will be apparent to those skilled in the art that various modifications may be made to the disclosed exemplary embodiment and methods and alternatives without departing from the spirit or scope of the disclosure. Thus, it is intended that the present disclosure covers the modifications and variations provided that they come within the scope of the appended claims and their equivalents.

What is claimed is:

1. A method for medical report-to-image navigation, comprising:
   retrieving, by a processor, a narrative report for at least one study including a plurality of images of a patient from a memory;
   determining, by the processor, text structure boundaries to identify and classify each text structure in the narrative report;
   determining, by the processor, image references in each text structure of the narrative report;
   extracting, by the processor, image references from text structures classified as including an image reference, wherein extracting image references includes: (i) extracting references where both series and image information is explicitly provided with a numeric value; (ii) extracting references where a series is referred to using an imaging scanning plane; (iii) extracting information where series information is included; and (iv) extracting information where a number over number pattern is provided;
   determining, by the processor, the at least one study to which each extracted image reference corresponds,
   rendering, by the processor, a report including the extracted image references and the at least one study to which the extracted image corresponds, and
   displaying, by the processor, the report, wherein the extracted image references are displayed as hyperlinks such that selecting one of the hyperlinks displays a corresponding image.

2. The method of claim 1, wherein the text structure is a sentence and determining sentence boundaries includes identifying end-of-sentence markers.

3. The method of claim 2, further comprising assigning end-of-sentence markers to a label including one of: i) not end of sentence; (ii) end of sentence, and sentence is a section header; (iii) end of sentence, and sentence is the last sentence in a paragraph; and (iv) end of sentence and sentence is neither a section header nor the last sentence in a paragraph.

4. The method of claim 1, wherein determining image references includes identifying image references including predetermined keywords indicating one of images, series, planar information, measurement values and date values.

5. The method of claim 1, wherein distinguishing image references from measurement and date values includes identifying image references including predetermined formats of measurements and dates, respectively.

6. The method of claim 1, wherein determining a study to which an extracted image reference corresponds includes one of identifying predetermined keywords indicating a prior study and identifying a predetermined formats of dates.

7. A system for medical report-to-image navigation, comprising:
   a memory including a narrative report for at least one study including a plurality of images for a patient; and
   a processor retrieving the narrative report from the memory, determining text structure boundaries to identify and classify each text structure in the narrative report, determining measurement and date values, extracting image references from text structures, wherein extracting image references includes: (i) extracting references where both series and image information is explicitly provided with a numeric value; (ii) extracting references where a series is referred to using an imaging scanning plane; (iii) extracting information where series information is included; and (iv) extracting information where a number over number pattern is provided, determining the at least one study to which each extracted image reference corresponds, rendering a report including the extracted image references and the at least one study to which the extracted image corresponds, and displaying the report, wherein the extracted image references are displayed as hyperlinks such that selecting one of the hyperlinks displays a corresponding image.

8. The system of claim 7, wherein the text structure is a sentence and the processor determines sentence boundaries by identifying end-of-sentence markers.

9. The system of claim 8, wherein the processor assigns the end-of-sentence markers to a label including one of: i) not end of sentence; (ii) end of sentence, and sentence is a section header; (iii) end of sentence, and sentence is the last sentence in a paragraph; and (iv) end of sentence and sentence is neither a section header nor the last sentence in a paragraph.

10. The system of claim 7, wherein the processor determines image references by identifying image references including predetermined keywords indicating one of images, series, planar information, measurement values and date values.

11. The system of claim 7, wherein the processor distinguishes image references from measurement and date values by identifying image references including predetermined formats of measurements and dates, respectively.

12. The system of claim 7, wherein the processor determines a study to which an extracted image reference corresponds by one of identifying predetermined keywords indicating a prior study and identifying a predetermined formats of dates.

13. The system of claim 7, wherein the processor distinguishes image references from measurement and date values to classify whether each text structure includes an image reference.

14. A non-transitory computer-readable storage medium including a set of instructions executable by a processor, the set of instructions operable to:
   retrieve a narrative report for at least one study including a plurality of images of a patient from a memory;
   determine text structure boundaries to identify and classify each text structure in the narrative report;
   determine image references in each text structure of the narrative report;
   analyze the text structures to identify and mark measurement and date values;
   extract image references from marked text structures, wherein extracting image references includes: (i) extracting references where both series and image information is explicitly provided with a numeric value; (ii) extracting references where a series is referred to using an imaging scanning plane; (iii) extracting information where series information is included; and (iv) extracting information where a number over number pattern is provided;
   determine the at least one study to which each extracted image reference corresponds;
   render a report including the extracted image references and the at least one study to which the extracted image corresponds; and
   display the report, wherein the extracted image references are displayed as hyperlinks such that selecting one of the hyperlinks displays a corresponding image.

* * * * *